United States Patent
Puckett

(10) Patent No.: US 10,966,907 B2
(45) Date of Patent: *Apr. 6, 2021

(54) METHOD AND APPARATUS FOR THE MANUFACTURE OF SOFTGELS

(71) Applicant: BARLEAN'S ORGANIC OILS, LLC, Ferndale, CA (US)

(72) Inventor: John Puckett, Ferndale, WA (US)

(73) Assignee: BARLEAN'S ORGANIC OILS, LLC, Ferndale, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/362,475

(22) Filed: Mar. 22, 2019

(65) Prior Publication Data

US 2019/0216685 A1 Jul. 18, 2019

Related U.S. Application Data

(60) Continuation of application No. 16/227,946, filed on Dec. 20, 2018, now abandoned, which is a continuation of application No. 15/673,789, filed on Aug. 10, 2017, now Pat. No. 10,195,115, which is a division of application No. 15/225,197, filed on Aug. 1, 2016, now Pat. No. 9,795,538, which is a continuation of application No. 14/926,217, filed on Oct. 29, 2015, now Pat. No. 9,433,559.

(60) Provisional application No. 62/073,761, filed on Oct. 31, 2014.

(51) Int. Cl.
| | | |
|---|---|---|
| A61J 3/07 | (2006.01) | |
| A61K 31/202 | (2006.01) | |
| A61K 31/201 | (2006.01) | |
| A61K 9/48 | (2006.01) | |
| A61K 31/00 | (2006.01) | |
| B30B 11/16 | (2006.01) | |
| B29C 43/08 | (2006.01) | |
| B29C 43/36 | (2006.01) | |

(52) U.S. Cl.
CPC ............... *A61J 3/07* (2013.01); *A61K 9/4808* (2013.01); *A61K 9/4825* (2013.01); *A61K 9/4833* (2013.01); *A61K 31/00* (2013.01); *A61K 31/201* (2013.01); *A61K 31/202* (2013.01); *B29C 43/08* (2013.01); *B29C 43/085* (2013.01); *B29C 2043/3678* (2013.01); *B30B 11/165* (2013.01)

(58) Field of Classification Search
CPC ...... A61J 3/07; A61J 3/005; A61J 3/10; A61J 2205/20; A61J 1/067; A61J 3/007; A61J 3/06; A61K 2300/00; A61K 31/202; A61K 9/4825; A61K 9/2873; A61K 9/4808; A61K 9/4833; A61K 9/2893; A61K 31/201; A61K 31/22; A61K 31/59; A61K 31/7076; A61K 33/04; A61K 33/26; A61K 9/2072; A61K 9/4883; A61K 31/00; A61K 9/0056; A61K 9/2886; A61K 9/4816; A61K 9/4858; A61K 9/4866; A61K 9/4891; A61K 31/135; A61K 31/137; A61K 31/167; A61K 31/19; A61K 31/192; A61K 31/20; A61K 31/519; A61K 35/60; A61K 45/06; A61K 47/10; A61K 47/36; A61K 47/42; A61K 8/11; A61K 9/16; A61K 9/2013; A61K 9/2018; A61K 9/2027; A61K 9/2031; A61K 9/2054; A61K 9/2068; A61K 9/2081; A61K 9/209; A61K 9/2095; A61K 9/282; A61K 9/2826; A61K 9/284; A61K 9/286; A61K 9/48; A61K 9/5084; A61K 9/51; A23P 10/30; A23L 29/284; A23L 27/72; A23L 33/12; A23L 33/16

See application file for complete search history.

(56) References Cited

U.S. PATENT DOCUMENTS

| | | | |
|---|---|---|---|
| 2,318,718 | A | 5/1943 | Scherer |
| 2,323,581 | A | 7/1943 | Weckesser |
| 2,497,212 | A | 2/1950 | Donofrio |

(Continued)

FOREIGN PATENT DOCUMENTS

| | | |
|---|---|---|
| GB | 2529599 | 2/2016 |
| JP | H5-51315 | 3/1993 |

(Continued)

OTHER PUBLICATIONS

International Search Report and Written Opinion dated Nov. 19, 2014 in PCT/US2014/039446 (4 Pages).

(Continued)

*Primary Examiner* — Audrea B Coniglio
*Assistant Examiner* — Audrea Buckley
(74) *Attorney, Agent, or Firm* — Fisherbroyles, LLP; Jason M. Pass

(57) ABSTRACT

Provided is a die roll for manufacturing softgels, a softgel, and methods for producing a softgel. The die roll includes a die roll surface and a pocket defined therein. The pocket includes a floor, an interior sidewall surface, a chamfer, and an exterior sidewall surface. The floor is recessed relative to the die roll surface and the interior sidewall surface is connected to the floor and extends above the die roll surface to the chamfer. The pocket also includes a landing surface that is elevated from the die role surface and connects the chamfer to the exterior sidewall surface of the pocket. The landing surface includes a taper (such that the landing surface tapers inwardly towards the pocket floor) and a radius (such that the landing surface is not flat). Also provided is a softgel having a trailing edge thickness that is at least about 40% the thickness of the softgel wall thickness.

20 Claims, 7 Drawing Sheets

(56) References Cited

U.S. PATENT DOCUMENTS

| | | | |
|---|---|---|---|
| 2,522,154 A | | 9/1950 | Asmussen |
| 3,038,282 A | | 6/1962 | Hansen |
| 4,026,437 A | | 5/1977 | Biddle |
| 4,594,926 A | | 6/1986 | Propheter |
| 5,146,730 A | | 9/1992 | Sadek |
| 5,342,188 A | | 8/1994 | Zimmermann |
| 5,459,983 A | | 10/1995 | Sadek |
| 5,535,885 A | | 7/1996 | Daniel |
| 5,761,886 A | | 6/1998 | Parkhideh |
| 5,827,535 A | * | 10/1998 | Stone ............... A61J 1/067 424/451 |
| 6,183,845 B1 | | 2/2001 | Ikemoto |
| 6,295,793 B1 | | 10/2001 | Takayanagi |
| 6,402,496 B2 | | 6/2002 | Ishikawa |
| 6,482,516 B1 | | 11/2002 | Sadek |
| 6,591,585 B2 | | 7/2003 | Stolz |
| 7,228,676 B2 | | 6/2007 | Davis |
| 7,490,456 B2 | | 2/2009 | Draisey |
| 8,621,764 B2 | | 1/2014 | Puckett |
| 9,364,441 B2 | | 6/2016 | Puckett |
| 9,433,559 B2 | * | 9/2016 | Puckett ............... A61J 3/07 |
| 9,795,538 B2 | | 10/2017 | Puckett |
| 2004/0253312 A1 | | 12/2004 | Sowden |
| 2005/0037065 A1 | | 2/2005 | Kirschner |
| 2005/0169983 A1 | | 8/2005 | Hassan |
| 2006/0292217 A1 | | 12/2006 | Schmidt |
| 2007/0212411 A1 | | 9/2007 | Fawzy |
| 2008/0057115 A1 | * | 3/2008 | Okamoto ............... A61K 31/20 424/452 |
| 2008/0295751 A1 | | 12/2008 | Shoup |
| 2009/0208608 A1 | | 8/2009 | Emerson |
| 2012/0058179 A1 | | 3/2012 | Altamar |
| 2014/0072625 A1 | | 3/2014 | Chidambaram |

FOREIGN PATENT DOCUMENTS

| | | |
|---|---|---|
| JP | 2003040768 A | 2/2003 |
| WO | 2007103557 | 9/2007 |
| WO | 2014190324 A2 | 11/2014 |
| WO | 2016069848 A1 | 5/2016 |

OTHER PUBLICATIONS

International Preliminary Report on Patentability dated Nov. 24, 2015 in PCT/US2014/039446 (7 Pages).

NonFinal Rejection issued in 14286850 dated Jan. 5, 2016 (15 pages).

Invitation to Pay Additional Fees dated Dec. 18, 2015 in PCT/US2015/057964 (2 pages).

International Search Report and Written Opinion dated Feb. 18, 2016 in PCT/US2015/057964 (13 Pages).

U.S. Appl. No. 14/926,217, filed Oct. 29, 2015, inventor John Puckett (297 pages).

PCT/US2015/057964 filed Oct. 29, 2015, Applicant Barlean's Organic Oils, LLC (80 pages).

U.S. Appl. No. 14/286,850, filed May 23, 2014, inventor John Puckett (277 pages).

Search and Examination Report issued in GB1522006.4 dated Jul. 14, 2016 (2 pages).

Canadian Office Action dated Sep. 2, 2016, in Canadian Patent Application No. 2,911,643 (3 pages).

Combined search and examination report issued in GB1617607.5 dated Dec. 7, 2016 (5 pages).

Extended European Search Report issued in EP15854433.8 dated Oct. 5, 2018 (11 pages).

JP Office Action issued in 2017-523542 dated Sep. 3, 2019 (5 pages).

\* cited by examiner

METHOD AND APPARATUS FOR THE MANUFACTURE OF SOFTGELS

CROSS-REFERENCE TO RELATED APPLICATIONS

This application is a continuation of U.S. patent application Ser. No. 16/227,946, filed Dec. 20, 2018, which is a continuation of U.S. patent application Ser. No. 15/673,789, filed Aug. 10, 2017, now U.S. Pat. No. 10,195,115, which is a divisional of U.S. patent application Ser. No. 15/225,197, filed Aug. 1, 2016, now U.S. Pat. No. 9,795,538, which is a continuation of U.S. patent application Ser. No. 14/926,217, filed Oct. 29, 2015, now U.S. Pat. No. 9,433,559, which claims the benefit of and priority to U.S. Provisional Application No. 62/073,761, filed Oct. 31, 2014. Each of U.S. patent application Ser. No. 16/227,946, U.S. patent application Ser. No. 15/673,789, U.S. patent application Ser. No. 15/225,197, U.S. patent application Ser. No. 14/926,217, and U.S. Provisional Application No. 62/073,761 are incorporated herein in their entirety.

TECHNICAL FIELD

The present disclosure relates generally to the field of manufacturing softgels, and in particular a rotary die for the manufacture of softgels, such as softgels having a predetermined shape. The present disclosure also relates to a method for making softgels using a rotary die system and process. The present disclosure also relates to a softgel having a superior seam thickness, such as at the trailing edge seam.

BACKGROUND

Softgels, such as softgel capsules, are formed by a variety or processes, including a rotary die encapsulation process. In the traditional rotary die process, encapsulation machines form two flexible gelatin sheets or ribbons, which are synchronously guided over rollers and fed to and between two dies. For example, a left and right ribbon each pass over rollers that feed the ribbons to (and between) two mated die rolls. The die rolls, whose surface architecture determines the size and shape of the resultant softgels, cut the softgel shells from the ribbons as the ribbons roll between the die rolls. A positive displacement pump simultaneously delivers the fill material into a heated wedge that sits between the rotary dies. The pump injects fill material, such as a liquid fill material, into the die cavities between ribbons just before the die rolls cut the ribbons and seals the two cut halves of the ribbon together to form a softgel. The softgels are then dried and allowed to harden.

While the rotary die manufacturing process is sufficient for making rounded or oblong softgels, using this process to manufacture shapes other than rounded or oblong forms has proven challenging. This is principally because the seam thickness where two halves of the softgel shells come together varies greatly. More particularly, the regions of gelatin ribbons that first enter die rolls form a leading edge on the resultant softgel, whereas the regions of the gelatin ribbons that follow behind form a trailing edge on the resultant softgel. Typically, the seam thickness at the trailing edge is only a small fraction of the wall thickness of the softgel. For example, the seam thickness of the trailing edge can be as little as 20% as thick as the wall thickness of the softgel. Hence, the thin seam thickness at the trailing edge cannot, for example, withstand certain manufacturing processes, such as those that seek to produce certain softgel shapes. Additionally, the thin seam at the trailing edge leads to breakage of softgel during handling of the product and leakage of the fill material. The thin seam thickness at the trailing edge can also be problematic for rounded or oblong softgels, such as during the manufacturing process and shipment.

SUMMARY

In certain example aspects described herein, a die roll is provided. For example, the die role includes a die roll surface, along with a pocket. The pocket includes a pocket floor, an interior sidewall surface, an exterior sidewall surface, and a chamfer. The pocket floor can be recessed relative to the surface of the die roll, and is connected to the interior sidewall surface. The interior sidewall surface extends above the die roll surface to the chamfer. The chamfer faces the interior of the pocket. Also included is a landing surface, which is elevated relative to the die role surface and connects the chamfer with the exterior sidewall surface of the pocket. The landing surface is tapered inwardly towards the pocket floor and forms a boundary of the pocket. In certain example aspects, the landing surface includes a radius.

In certain example aspects described herein, also provided is a process for making a softgel, such as a softgel having an increased thickness at the trailing edge of the softgel when compared to conventional softgels. The process can also be used, for example, to make softgels having a predetermined shape, such as a heart shape. For example, two soft film ribbons are formed from a film-forming composition. The ribbons are then passed between two mated dies, each mated die being configured as described herein. For example, each die includes, among other features, a landing surface that is tapered inward, along with a chamfer that is connected to the interior sidewall surface of the pocket and that faces the interior of the pocket. In certain aspects, the landing surface of the die includes a radius. As the ribbons pass between the two mated die rolls, the process includes simultaneously cutting the ribbons to form two complementary softgel shell halves, heat-sealing the softgel shell halves to form a softgel body, and filling the softgel body with a fill material.

In certain example aspects described herein, also provided is a softgel. For example, the softgel has a softgel body. The body includes, for example, a seam and a softgel body wall. In certain example aspects, the seam has a thickness that is at least about 40% of the thickness of the wall along the entire length of the seam. In certain example aspects described herein, the seam includes a leading edge seam and a trailing edge seam, with the trailing edge seam being at least about 40% the thickness of the body wall.

In certain example aspects, the softgel has a first softgel shell half and a second softgel shell half, the softgel shell halves being complementary to each other and each softgel shell half including a softgel wall. The softgel wall of each softgel half, for example, includes a thickness corresponding to a distance between an interior wall surface of the softgel wall and an exterior wall surface of the softgel wall. The softgel also includes a seam, the seam being formed at the juncture of the first softgel shell half and the second softgel shell half. The seam, for example, includes a trailing edge having a trailing edge thickness corresponding to a distance from an outer seam edge of the trailing edge and an inner seam edge of the trailing edge. The trailing edge thickness, for example, is at least 40% of the softgel wall thickness of either of the first softgel shell half or the second softgel shell half. In certain example aspects, the softgel as described herein has a predetermined shape, such as a heart shape.

These and other aspects, objects, features, and advantages of the example embodiments will become apparent to those having ordinary skill in the art upon consideration of the following detailed description of illustrated example embodiments. Related methods of operation are also provided. Other apparatuses, methods, systems, features, and advantages of the die roll, softgel, and process for making the softgel, will be or become apparent to one with skill in the art upon examination of the following figures and detailed description. It is intended that all such additional apparatuses, methods, systems, features, and advantages be included within this description, be within the scope of die roll, softgel, and process for making the softgel, be protected by the accompanying claims.

DETAILED DESCRIPTION OF EXAMPLE EMBODIMENTS

Figure 1B:
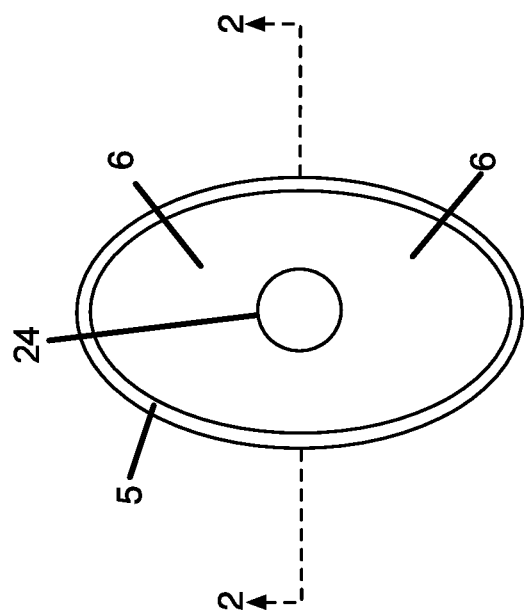
FIG. 1B is an illustration depicting a top view of an example pocket of the die roll, in accordance with certain example embodiments.

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are references to the same embodiment. And, such references mean at least one of the embodiments.

Further, reference to an "embodiment" or "example embodiment" means that a particular feature, structure, or characteristic described in connection with the embodiment is included in at least one embodiment of the-disclosure. Similarly, the appearance of the phrase "in certain embodiments" in various places herein are not necessarily all referring to the same embodiment, nor are separate or alternative embodiments mutually exclusive of other embodiments. Moreover, various features are described which can be exhibited by some embodiments and not by others. Similarly, various requirements are described which can be requirements for some embodiments but not other embodiments.

The terms used herein generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms can be highlighted in quotation marks. The use of such highlighting has no influence on the scope and meaning of a term. Rather, the scope and meaning of a term is the same, in the same context, whether or not it is highlighted.

It will be appreciated that the same thing can be said in more than one way. Hence, alternative language and synonyms can be used for any one or more of the terms discussed herein. Nor is any special significance to be placed upon whether or not a term is elaborated or discussed herein. Synonyms for certain terms can also be provided herein. A recital of one or more synonyms does not exclude the use of other synonyms, for example. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

As used herein, the singular forms "a," "an" and "the" include plural referents unless the context clearly dictates otherwise. Thus, for example, reference to a "softgel" includes aspects having two or more softgels unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance can or cannot occur, and that the description includes instances where said event or circumstance occurs and instances where it does not.

Overview

The example embodiments described herein provide a die roll for use in manufacturing a softgel, along with a process for manufacturing a softgel using the die roll. The example embodiments described herein also provide a softgel product produced from the apparatus and process described herein.

The example embodiments described herein also provide a softgel with a superior seam thickness, such as at the trailing edge seam.

As used herein, a "softgel" refers to a soft dosage form, such as a gelatin-based capsule, that is provided as a single dosage form. In certain example embodiments, the softgel includes a liquid fill, such as a suspension or semisolid, which is enveloped by two halves of a gelatin shell to form a single, hermitically sealed dosage form. As one skilled in the art will appreciate, the gelatin shell can be composed of gelatin, a plasticizer, and water, and can also include other ingredients such as preservatives, coloring, flavorings, opacifying agents, sweetening agents, acids, salts, medicaments, or other agents to achieve a desired dosage effect.

As used herein, a "die roll" refers to one of a mated pair of dies that are suitable for making and filling softgel capsules. Each die roll of the mated pair, for example, contains on its surface a series of one or more depressions or "pockets" for the formation of a softgel shell half. The series of pockets on the surface of each die roll are arranged, for example, in rows extending along the axial length of the die roll, with the series of rows also extending around the die roll. In certain examples, the rows can be configured in a pattern, such as an offset pattern, to maximize the number of pockets on the surface of the die.

In certain examples, the pocket includes a floor, an interior sidewall surface, an exterior sidewall surface, and a chamfer. Also included is a "land," which includes a "landing surface," the landing surface being elevated relative to the surface of the die roll. Hence, the landing surface represents the location of the pocket on one die roll that makes contact with the other, mated die roll during the manufacture of a softgel. That is, during the encapsulation process, the landing surface of one die contacts the landing surface of the matching or "mated" die roll in order to cut the gelatin ribbons as the ribbons pass between the two mated dies. For example, two soft gelatin film ribbons are passed between two die mated die rolls as described herein. As the ribbons pass between the two mated dies, the die rolls, as configured herein, cut the ribbons via the mated landing surfaces to form two complementary softgel shell halves. The two softgel shell halves are then heat-sealed to form a softgel body. The body is injected with fill material, thus resulting in the filled softgel. The juncture of the two complementary softgel shell halves forms a softgel seam on the softgel body.

Because the landing surface is responsible for cutting the softgel shells, the shape of the landing surface around the pocket determines the shape of the resultant softgel. For example, the landing surface forms a boundary defining the shape of the pocket. In other words, the landing surface circumscribes the edge of the pocket. Hence, the shape of the landing surface—when brought into contact with the landing surface on the mated die—determines the shape of the resultant softgel. As those skilled in the art will appreciate, the landing surface of the pocket can be configured in a variety of predetermined shapes, such as round, oblong, or other suitable shapes. In certain examples, the shape of the softgel is that of a heart shape or heart symbol ideograph. In certain examples, the shape includes a point.

As described herein, the landing surface of the land can be tapered inwards towards the interior of the pocket, such as towards the pocket floor. That is, in one aspect, the landing surface can be slanted inward towards the pocket floor, for example, so that the inner edge of the landing surface near the pocket interior is slightly lower than the exterior edge of the landing surface. Additionally, the landing surface of the pocket can be associated with a bevel or "chamfer." The chamfer, for example, can be located just below the interior edge of the landing surface and thus connects the interior edge of the landing surface with the interior wall of the pocket. In certain examples, the landing surface includes a "round" or "radius" that results in a curved or rounded landing surface.

By configuring the die roll pocket, for example, to include a tapered landing surface and associated chamfer as described herein—along with a radius—a softgel can be produced having a substantially thicker seam along portions of the softgel seam (as compared to conventional softgels). For example, the softgels as described herein have a trailing edge seam thickness that can be substantially thicker than the trailing edge thickness of conventional softgels. In certain examples, the leading edge seam thickness can also be thicker than the leading edge of conventional softgels.

Without wishing to be bound by any particular theory, it is believed that the tapering and rounding of the landing surface—such as in conjunction with the chamfer and radius, for example—directs each gelatin film inwardly towards the center of the softgel when the opposing landing surfaces of the two mated dies come together during the manufacture of a softgel. Hence, it is believed that more gelatin film aggregates and collects at the seam during the film-cutting process with die rolls configured as described herein, thus resulting in a substantially thicker seam during the manufacturing process and in the finished softgel product.

In certain examples, provided is a softgel with a substantially thicker seam than conventional softgels. That is, the seam where two complementary softgel shells come together forms a thickness that can be substantially greater than the corresponding seam in conventional softgels. For example, a conventional softgel can have trailing edge thickness that is only about 20% of the softgel wall thickness. In contrast, in certain examples provided herein the trailing edge of the softgel has an unexpectedly increased thickness of at least about 40% of the softgel wall thickness. In some examples, an increased thickness of at least about 60% is observed, though even greater thicknesses can be observed for the trailing edge of the softgel described herein. Hence, the trailing edge thickness of the softgel described herein can be, in certain examples, unexpectedly about 2-3 times thicker (or more) than the trailing edge thicknesses observed in conventional softgels. In certain examples, other regions of the seam, including the leading edge of the seam, have an increased thickness.

Increasing the seam thickness as described herein confers several advantages, both during the manufacturing process and in the resultant softgel product. For example, during the softgel manufacturing process, the softgel shell halves are subjected to pressure as they are cut. Additionally, the softgel body is subjected to an internal, expansion pressure as a fill material is injected into the softgel body. Without wishing to be bound by any particular theory, it is believed that the design of the die described herein allows the softgel body to withstand greater pressures, such as during manufacture of the softgel. In other words, it is believed that directing the gelatin film inwardly towards the center of the softgel permits the softgel film—and softgel body—to withstand higher pressures, such as during the cutting and injection processes of the softgel manufacturing process, respectively.

By providing for and facilitating increased pressures during the cutting and injection processes, producing softgels having specific, predetermined shapes as described herein is made substantially and unexpectedly easier. For example, manufacturing conventional softgels with points or other non-rounded seams is extremely challenging, as the cutting and/or injection process leads to breakage of failure of the softgel body. Such breakage and failures are improved, however, when the resultant softgel seam, such as the trailing edge seam, is substantially thicker as described herein. Hence, shapes such as hearts and/or other shapes having points, for example, are readily made by the methods and processes described herein. Additionally, shapes such as rounded or oblong softgels produced by the die roll and methods described here have advantageously thicker seams as compared to conventional softgels.

For softgel products with thicker seams, such as those made according to the apparatus, methods, and processes described herein, these softgels have significant advantages over conventional softgels. For example, the thicker seam leads to less breakage of the softgel, such as during manufacture and while handling of the softgel during shipment or by the end consumer. This is particularly true for softgels having certain shapes, such as pointed- or non-rounded regions, as these regions are often more included to break. Less breakage, for example, leads to less leakage of the fill material, which in turn reduces product waste. For example, product leaking can contaminate an entire bottle or batch of finished softgel product, causing the consumer to discard the entire contents of a bottle, for example. These and other advantages will be apparent to those skilled in the art, based on the example embodiments described herein.

Example Embodiments

The example embodiments described herein provide a die for encapsulation, a process and method for encapsulation, a product of the method and process, and a softgel.

Figure 1A:
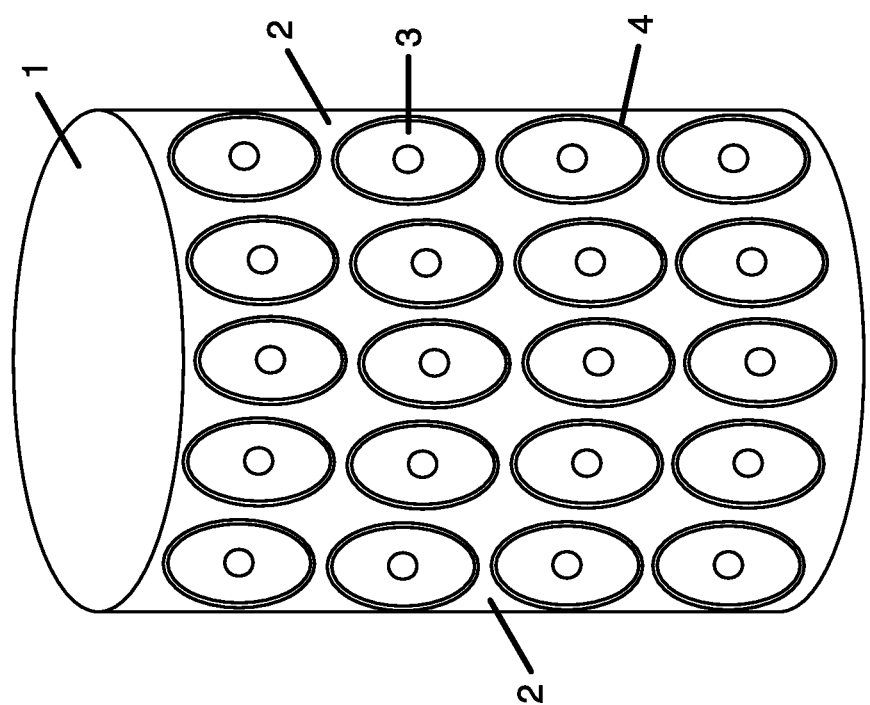
FIG. 1A is an illustration depicting an example die roll for use in manufacturing a softgel, in accordance with certain example embodiments.

Turning to the drawings, FIG. 1A is an illustration depicting an example die roll for use in manufacturing a softgel, in accordance with certain example embodiments. As shown, the die role 1 can be substantially cylindrical in shape. The die roll 1 comprises a die roll surface 2 having at least one die roll pocket 3 being defined in and/or thereon the die roll surface 2. In one aspect, the at least one die roll pocket can comprise a plurality of die roll pockets 3 interspersed on the die roll surface. For example, the die roll 1 can contain multiple pockets 3 that are arranged in a predetermined pattern and/or an array across the die roll surface 2.

The die roll 1 can be any suitable width from end to end—as well as any suitable diameter—that is adaptable and configurable for use in conventional rotary die encapsulation machines as described herein or known in the art. In certain example embodiments, the width of the die roll 1 can be about 25 cm, such as about 23, 24, 25, 26, or 27 cm long. In certain example embodiments, the diameter of the die roll 1 can be about 15 cm, such as about 13, 14, 15, 16, or 17 cm.

In certain example embodiments, the die roll 1 can include from about 5 to about 30 rows of pockets 3, with each row including from 25 to 50 pockets 3. In certain example embodiments, the die roll 1 can include from about 7 to about 22 rows of pockets 3, with each row including from 30 to 46 pockets 3. In certain example embodiments, the shape of the pocket 3 can determine the most efficient arrangement of the pockets 3 on the die roll surface 2. For example, where multiple pockets 3 are disposed on the die roll surface 2, the pockets 3 can be arranged so as to maximize the number of pockets 3 on the die roll surface 2, so as to produce a maximum number of softgels.

As those skilled in the art will appreciate, the die roll 1 can be used and/or adapted for use in conjunction with a variety of soft gelatin encapsulation machines. That is, the die roll 1 can be adapted for use in conventional rotary die soft gelatin encapsulation machine similar to those known in the art. For example, within a conventional softgel encapsulation machine, the die roll 1 can be aligned with and mated to an opposing die roll having the same or similar configuration. The two, mated die rolls rotate in opposite directions as part of the encapsulation machine, and—as gelatin ribbons pass though the mated die roll pair—the mated die rolls cut and fill the softgel body with a fill material. The conventional gelatin encapsulation machine can include any other components needed to manufacture a softgel, such as a heating wedge, nip, injection pump, gelatin film presses, feeders, guide rollers, and the like, as those of skill in the art will appreciate. The die roll 1 can also be constructed out of one or more suitable materials known in the art, such as aluminum, brass, hardened steel, bronze, or combinations thereof.

FIG. 1B is an illustration depicting a top view of an example pocket 3 of the die roll 1, in accordance with certain example embodiments, such as a pocket 3 defined in and/or on the die roll surface 2 as described herein. In one aspect, each pocket can be defined by a sidewall extending around the perimeter of the pocket and extending outwardly away from the die roll surface. The sidewall comprises an interior sidewall surface 7 and an opposed exterior sidewall surface 9. An end wall or land 4 can be formed between the interior sidewall surface and the exterior sidewall surface. In use, described more fully below, the land of a first die roll can be complementary to the land on a mated die roll, for example. In another aspect, each land comprises a landing surface 5, the landing surface being elevated relative to the surface of the die roll. Hence, the landing surface represents the location on one die roll that makes contact with another, mated die roll during the manufacture of a softgel.

A pocket floor 6 can be formed adjacent to the interior sidewall surface 7. In one aspect, the pocket floor can be recessed relative to the die roll surface, whereas the landing surface 5 can be elevated above the die roll surface. The landing surface 5 of the land 4 can circumscribe the pocket 3, thereby forming a boundary of the pocket 3. As is shown in FIG. 1B, for example, the landing surface 5 runs along at least a portion of the border of the pocket 3. Hence, as those skilled in the art will appreciate, changing the shape or path of the land 4 and the associated landing surface 5 around the pocket 3 can result in changing the shape of the softgel shell half that is cut from a gelatin ribbon.

In certain example embodiments, the pocket floor 6 can include a vent opening 24. Without wishing to be bound by any particular theory, the vent opening is believed to allow air to be displaced out of the pocket 3, such as when the softgel body is being expanding into the pocket 3 during the fill injection process. The vent opening, for example, can also prevent the softgels from sticking to the die roll 1 during manufacture of the softgels. For example, it is believed that the vent opening can prevent a vacuum from being formed within the pocket 3 as the gelatin films fill the pocket during expansion of the softgel body during the manufacturing process. By relieving such a vacuum, for example, the vent opening allows the softgels to fall freely from the mated die rolls after formation of the softgels.

Figure 2:
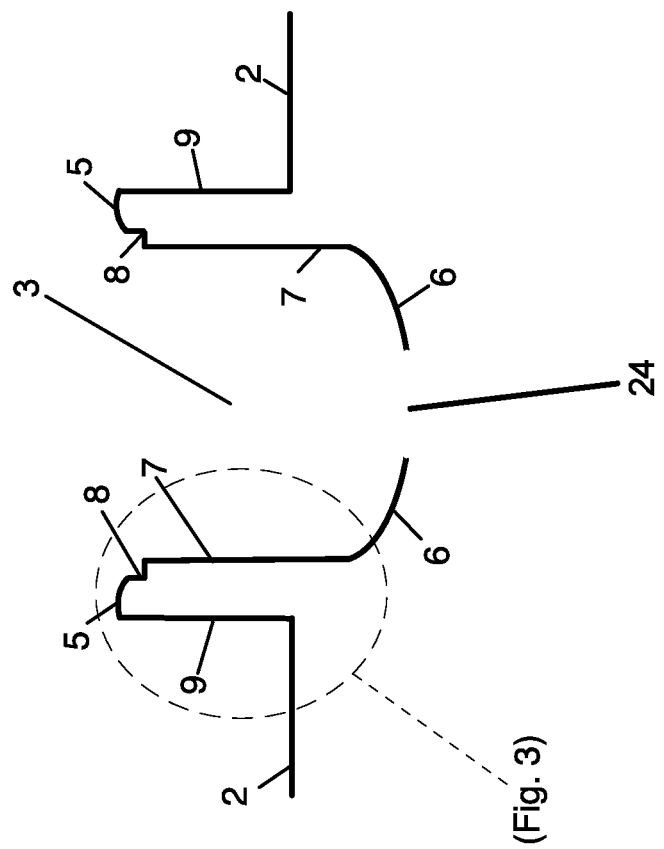
FIG. 2 is cross-sectional view of an example pocket, illustrating the profile taken through the line 2-2 as shown in FIG. 1B, in accordance with certain example embodiments.

FIG. 2 is cross-sectional view of an example pocket 3, illustrating the profile taken through the line 2-2 as shown in FIG. 1B, in accordance with certain example embodiments. In FIG. 2, an example die roll surface 2 is illustrated along with a pocket 3. The pocket 3 can be defined by the pocket floor 6, the interior sidewall surface 7, a chamfer 8, and the exterior sidewall surface 9. In certain example embodiments, the floor 6 can be recessed relative to the die roll surface 2. The interior sidewall surface 7 of the pocket 3 is connected to the pocket floor 6 and extends above the die roll surface 2 to the chamfer 8. Further, the pocket 3 of the die roll 1 comprises the landing surface 5 being elevated from the die role surface 2 and connecting the chamfer 8 to the exterior sidewall surface 9 of the pocket 3. In one aspect, the landing surface 5 can be tapered inwardly towards the pocket floor 6. The landing surface 5, for example, forms a boundary of the pocket 3.

As shown in FIG. 2, the pocket floor 6 transitions, for example, into the interior sidewall surface 7. The transition, for example, can be configured as desired, such as to be abrupt or more evenly disposed. For example, the floor 6 can transition to the interior sidewall surface 7 at the periphery or edge of the floor 6. As is also shown, in certain example embodiments the pocket floor 6 can be recessed relative to the die roll surface 2. That is, the pocket floor 6 can represent a depression relative to the die roll surface 2. As those skilled in the art will appreciate, the dimensions and configuration of the pocket 3, for example, are configurable and can hence be determined based on the desired dimensions of the final softgel product. Those skilled in the art will also appreciate that the drying and curing process will also affect the dimensions and shape of the final softgel product.

In certain example embodiments, the depth of the recess of the pocket floor 6 can vary across the pocket floor 6, and can be configurable based on the desired shape and size of the resultant softgel. For example, the recess can be deeper towards the center of the pocket floor 6 as compared to where the pocket floor 6 transitions into the interior sidewall surface 7. In certain example embodiments, the depth of the pocket floor 6, relative to the die roll surface 2, can be between about 2 and 10 mm, such as about 2, 3, 4, 5, or 6 mm. In certain example embodiments, the depth of the pocket floor 6, relative to the die roll surface 2, can be at least about 5.5, 5.6, 5.7, 5.8, 5.9, or 6.0 mm. In certain example embodiments, the depth of the pocket floor 6, relative to the die roll surface 2, can be at least about 5.8 mm. In certain example embodiments, the depth of the pocket floor 6, such as from the landing surface 5 to the floor 6, can be about 100 to about 400 thousandths of an inch, such as about 100, 200, 300, or 400 thousandths of an inch. In certain example embodiments, the depth of the pocket floor 6, such as from the landing surface 5 to the pocket floor 6, can be about 200 thousandths of an inch. As those skilled in the art will appreciated, the width and length of the floor can also be configurable based on the desired shape of the final softgel product. For example, the width of the floor 6 can be between about 10 and 20 mm, such as about 12, 13, 14, 15, 16, or 17 mm. Similarly, the length of the floor 6 can be between about 10 and 20 mm, such as about 12, 13, 14, 15, 16, or 17 mm.

The interior sidewall surface 7 of the pocket, for example, extends outwardly from the pocket floor 6 to above the die roll surface 2, where it eventually connects to the chamfer 8. The length of the interior sidewall surface 7 can be configurable, for example, and can be determined based on the desired depth of the pocket floor as described herein. As shown, the pocket floor 6, the interior sidewall surface 7, and the chamfer 8 collectively form a pocket interior of the die roll pocket 3. That is, the pocket floor 6, the interior sidewall surface 7, and the chamfer 8, for example, define the boundaries of a space within the pocket 3, the space corresponding to the pocket interior. The chamfer 8, for example, faces the interior of the pocket, as illustrated in FIG. 2. As those skilled in the art will appreciate, the pocket interior represents the region that receives and forms half of a softgel shell during the manufacturing process.

In addition to the features described above, and with continued reference to FIG. 2, the example pocket 3 includes an exterior sidewall surface 9. The exterior sidewall surface 9, for example, originates at the die roll surface 2 and extends outwardly relative to the die roll surface 2. In certain example embodiments, the exterior sidewall surface 9 can form about a 90° angle with the die roll surface 2. In other example embodiments, the exterior sidewall surface can be at an acute angle relative to the die roll surface. For example, the exterior sidewall surface 9 can be slightly angled towards the pocket interior or away from the pocket interior. The exterior sidewall surface 9 can be any configurable length compatible with making a softgel, such as about 0.5, 1.0, 2.0, 3.0, 4.0, 5.0, 6.0, 7.0, 8.0, 9.0, or 10.0 mm, such as measured from the die roll surface 2 to the exterior edge 10 of the landing surface 5. In certain example embodiments, the exterior sidewall surface 9 can be about 6.0 mm in length from the die roll surface 2 to the exterior edge 10 of the landing surface 5, such as about 5.6, 5.7, 5.8, 5.9, 6.0, 6.1, 6.2, 6.3, or 6.4 mm in length. In certain example embodiments, the exterior sidewall surface 9 can be about 1.0 mm in length from the die roll surface 2 to the exterior edge 10 of the landing surface 5, such as about 0.5, 0.6, 0.7, 0.8, 0.9, 1.0, 1.1, 1.2, 1.3, or 1.5 mm in length.

As shown, the landing surface 5 connects the exterior sidewall surface 9 to the chamfer 8. That is, the landing surface 5 spans the region between the exterior sidewall surface 9 and the beginning of the chamfer 8. In certain example embodiments, the landing surface 5 comprises a radius or round, as described further below. In certain example embodiments, the width of the land 4 can be about 0.5 to 1.5 mm, such as 0.5, 0.6, 0.7, 0.8, 0.9, 1.0, 1.1, 1.2, 1.3, 1.4, or 1.5 mm. For example, at a given point on the exterior sidewall surface 9, the distance between the exterior sidewall surface 9 and the interior sidewall surface 7 can be about 0.5, 0.6, 0.7, 0.8, 0.9, 1.0, 1.1, 1.2, 1.3, 1.4, or 1.5 mm. In certain example embodiments, the width of the land 4 is about 1.0 mm. In certain example embodiments, the width of the land can be about 30 to about 50 thousandths of an inch, such as about 40 thousandths of an inch.

Figure 3:
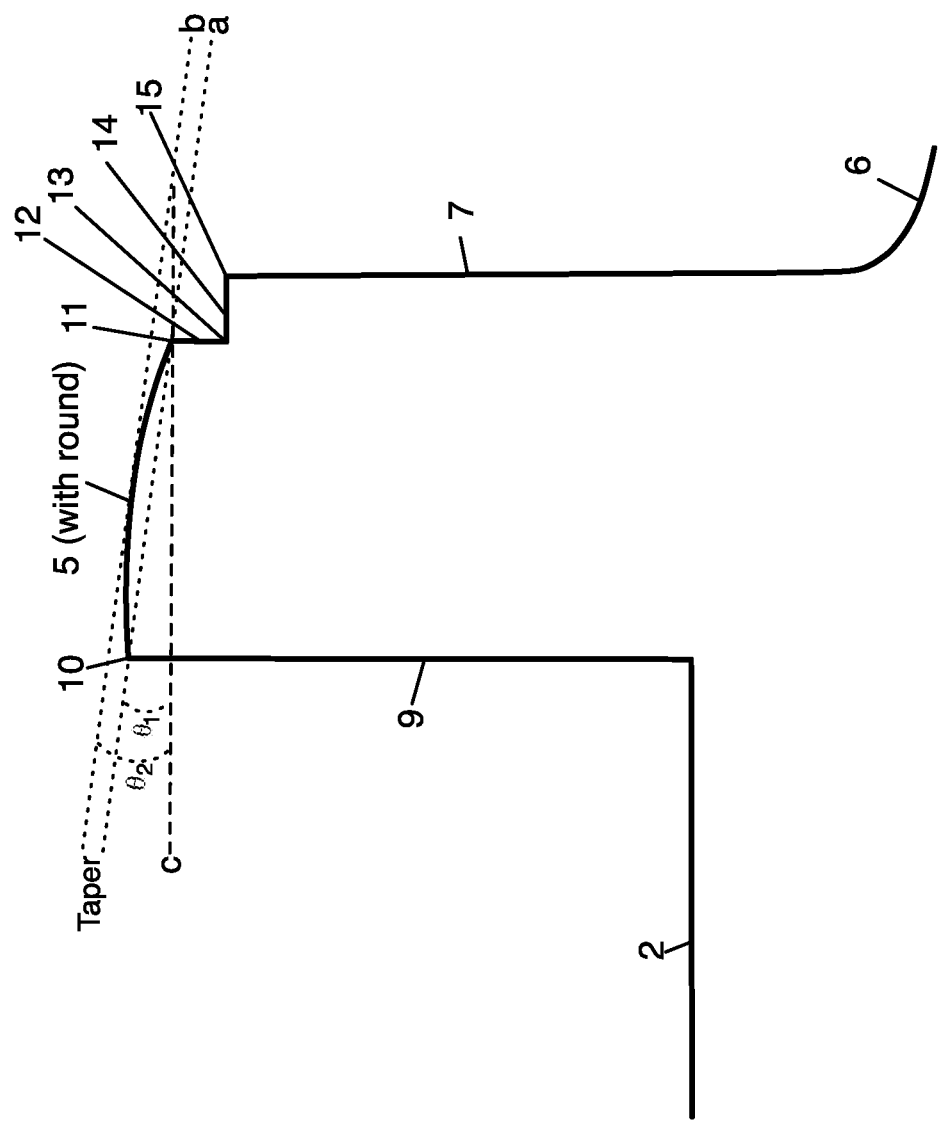
FIG. 3 is an enlarged view of an example pocket cross-section (as indicated on FIG. 2), in accordance with certain example embodiments.

FIG. 3 is an enlarged view of an example pocket cross-section (as indicated on FIG. 2), in accordance with certain example embodiments. As shown, the landing surface 5 comprises an exterior edge 10, formed where the exterior sidewall surface 9 meets the landing surface 5. The landing surface 5 further comprises an interior edge 11, formed where the landing surface 5 meets a chamfer wall 12 of the chamfer 8. The chamfer wall 12, for example, extends downward to a chamfer notch 13, where the chamfer wall 12 meets a chamfer floor 14. The chamfer floor 14, for example, extends from the chamfer notch 13 towards the pocket interior to a chamfer edge 15, the chamfer edge 15 representing the region of the chamfer 8 that meets and transitions to the interior sidewall surface 7. In one aspect, at least a portion of the chamfer wall can be substantially parallel to the interior sidewall surface 7 and/or the exterior sidewall surface 9. In another aspect, at least a portion of the chamfer floor can be substantially normal to the chamfer wall 12. Alternatively, at least a portion of the chamfer floor 14 can be at an acute angle relative to the chamfer wall 12.

Optionally, at least a portion of the chamfer floor 14 can be substantially parallel to the die roll surface 2 adjacent to the exterior sidewall surface 9.

As those skilled in the art will appreciate, the size and dimensions of the chamfer 8 can vary depending on the size of the softgel to be produced. In certain example embodiments, the length of the chamfer floor 14, such as from the chamfer notch 13 to the chamfer edge 15 can be about 1.0 to about 7.0 thousandths of an inch. For example, the length of the chamfer floor 14, such as from the chamfer notch 13 to the chamfer edge 15, can be about 5.0 thousandths of an inch. In certain example embodiments, the length of the chamfer wall 12, such as from the chamfer notch 13 to the interior edge 11 of the landing surface 5, can be about 1.0 to about 7.0 thousandths of an inch. In certain example embodiments, the length of the chamfer wall 12, such as from the chamfer notch 13 to the interior edge 11 of the landing surface 5, can be about 5.0 thousandths of an inch.

In certain example embodiments, the exterior edge 10 of the landing surface 5 can be rounded or smooth, so as not to result in a fine edge on the exterior edge 10 of the landing surface 5. In other example embodiments, the exterior edge 10 need not be rounded or smooth, thus resulting in a fine or sharp edge on the exterior edge 10 of the landing surface 5. In certain example embodiments, the interior edge 11 can be rounded or smooth, so as not to result in a fine or sharp edge on the interior edge 11 of the landing surface 5. In other example embodiments, the interior edge 11 need not be rounded or smooth, thus resulting in a fine or sharp edge on the interior edge 11 of the landing surface 5.

Continuing with reference to FIG. 3, in one aspect, the landing surface 5 comprises a taper, with the angle of the taper, for example, directed towards the pocket floor 6. That is, the landing surface 5 can slant downward from the exterior edge 10 of the landing surface 5 to the interior edge 11 of the landing surface 5, and towards toward the pocket floor 6. In FIG. 3, the dotted lines ("a" and "b"), for example, illustrate an example taper that is associated with the landing surface 5 as described herein. The dotted line "a," for example, illustrates a plane of a taper that runs from the elevation of the exterior edge 10 of the landing surface 5 to the elevation of the interior edge 11 of the landing surface 5. Dotted line "b," for example, represents a plane that is roughly parallel to line "a," and hence is also representative of the taper (such as when a round is present as discussed below, for example).

In certain example embodiments, the degree of the taper angle depends, for example, on the elevation of the exterior edge 10 of the landing surface 5 relative to the interior edge 11 of the landing surface 5, as well as the distance between these two points. That is, for a given length between the exterior edge 10 of the landing surface 5 and the interior edge 11 of the landing surface 5, the more the exterior edge 10 is elevated above the interior edge 11, the greater the angle of the taper. For example—and for a given length between the exterior edge 10 and the interior edge 11—the exterior edge 10 of the landing surface 5 can be elevated above the interior edge 11 by extending the exterior sidewall surface 9 lengthwise away from the die roll surface 2 by and above the chamfer wall 12. In certain example embodiments, the taper can be slight, such as when the exterior edge 10 is about 0.1 mm to about 0.3 mm above the interior edge 11, such as 0.1, 0.2, or 0.3 mm. For example, in certain embodiments, the exterior edge 10 can be elevated by about 0.10, 0.11, 0.12, 0.13, 0.14, 0.15, 0.16, 0.17, 0.18, 0.19, 0.20, 0.21, 0.2, 0.22, 0.23, 0.24, 0.25, 0.26, 0.27, 0.28, 0.29, or 0.30 mm above the interior edge 11 to form the taper. In certain example embodiments, the exterior edge 10 can be elevated above the interior edge 11 by about 7 to about 10 thousandths of an inch. For example, the exterior edge 10 can be elevated above the interior edge 11 by about 3.0 to about 4.0 thousandths of an inch.

In certain example embodiments, the taper can be greater, such as by elevating the exterior edge 10 by about 0.30 mm to about 0.60 mm above the interior edge 11. For example, the exterior edge 10 can be elevated by about 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, or 0.60 mm above the interior edge 11. If an even greater taper is needed, the exterior edge 10 can be elevated by about 0.6, 0.7, 0.8, 0.9, or 1.0 mm, for example.

With regard to the distance (or length) between the exterior edge 10 and the interior edge 11, which corresponds to the length of the landing surface 5, the distance can be any configurable distance suitable for cutting softgel films. For example, the length between the exterior edge 10 and the interior edge 11 can be about 30.0 to about 100.0 thousandths of an inch, such as about 35, 36, 37, 38, 39, 40, 41, 42, 43, 44, 45, 46, 47, 48, 49, 50, 51, 52, 53, 54, 55, 56, 57, 58, 59, or 60 thousandths of an inch. In certain example embodiments, the length between the exterior edge 10 and the interior edge 11 can be about 44 thousandths of an inch.

In certain example embodiments, the landing surface 5 can also be associated with a "round" or radius. That is, in one aspect, the landing surface 5 between the exterior edge 10 and the interior edge 11 can be arcuate in shape. For example, in this aspect, the landing surface 5 need not be flat, but rather the landing surface 5 can bow outwardly, such as is illustrated with the rounded landing surface 5 in FIG. 3. In other words, the landing surface 5, in certain example embodiments, can be a rounded surface, such as rounded surface that includes a region that bows outwardly away from the die roll 1, such as away from the die roll surface 2. In certain example embodiments, the radius or round can be curvilinear, without necessarily conforming to an exact radius. In certain example embodiments, the round can be elliptical. In certain example embodiments, the radius (or round) can extend outwardly from the plane of the landing surface 5 by a radius of about 10, 20, 30, 40 or 50 thousandths of an inch. For example, the radius can be about 20 thousandths of an inch.

In certain example embodiments, the taper of the landing surface 5 can be determined and/or expressed as an angle "θ," which corresponds to the downward angle of the taper (as shown in FIG. 3, line "a" and parallel line "b") towards the pocket floor 6. That is, in certain example embodiments, the angle θ can be determined by measuring or calculating the angle between the plane of the taper (line "a" or "b") and an imaginary line that runs horizontally across the land 4 (such as shown in FIG. 3). In other example embodiments, the angle θ can be determined by measuring or calculating the angle between the plane of the taper (line "a" or "b") and the die roll surface 2 adjacent to the pocket 3. For example, and with reference to FIG. 3, the angle $\theta_1$ of the taper can be determined by measuring or calculating the angle between dashed line "c" and dotted line "a," with line "a" representing the plane of the taper, and with line "c" being substantially parallel to the die roll surface 2.

Additionally or alternatively, the angle $\theta_2$ of the taper can be determined or estimated, such as when a round or radius is present, by measuring or calculating the angle created between dashed line "c" and dotted line "b," with line "b" representing the plane of the taper determined above the round. As those skilled in the art will appreciate, because the planes represented by lines "a" and "b" are roughly parallel, such as is shown in FIG. 3, the angles $\theta_1$ and $\theta_2$ should be roughly the same (equal or about equal), each of which thus corresponding to the downward angle of the taper θ as described herein. In certain example embodiments, the downward angle of the taper θ as described herein can be about 5° to about 25°, such as 5, 6, 7, 8, 9, 10, 11, 12, 13, 14, 15, 16, 17, 18, 19, 20, 21, 22, 23, 24, or 25°. In certain example embodiments, the downward angle of the taper θ as described herein can be can be 6° to 15°. In certain example embodiments, the downward angle of the taper θ as described herein can be at least about 7°.

As described herein, without wishing to be bound by any particular theory, it is believed that the taper of the landing surface 5, such as in combination with the chamfer 8 and the radius or round, facilitates directing the gelatin films inward during the gelatin film cutting process. It is believed that this in turn increases the seam thickness, thus aiding in the manufacturing of the softgels as described herein. The increased seam thickness also improves the quality of the final softgel product—verses conventional softgel products—as described herein.

Figure 4A:
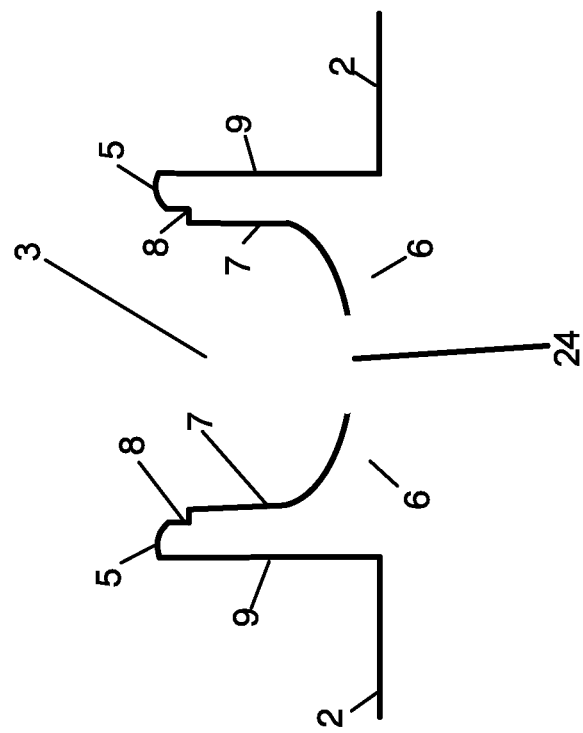
FIG. 4A is an illustration depicting a cross-sectional view of an example pocket having a pocket floor that is level with the die roll surface, in accordance with certain example embodiments.
Figure 4B:
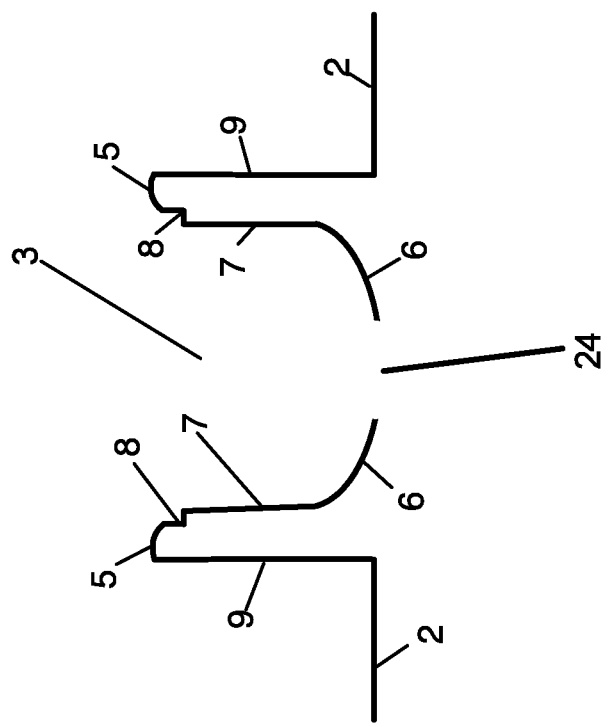
FIG. 4B is an illustration depicting a cross-sectional view of an example pocket having a pocket floor that is elevated above the die roll surface 2, in accordance with certain example embodiments.

FIG. 4A is an illustration depicting a cross-sectional view of an example pocket 3 having a pocket floor 6 that is level with the die roll surface 2, in accordance with certain example embodiments. That is, in certain example embodiments, the pocket floor 6 need not be recessed relative to the die roll surface 2. For example, the pocket floor 6 can be roughly level with the die roll surface as depicted in FIG. 4A. FIG. 4B is an illustration depicting a cross-sectional view of an example pocket 3 having a pocket floor 6 that is elevated above the die roll surface 2, in accordance with certain example embodiments. That is, the pocket floor 6 can be elevated above the die roll surface 2. In either case, such as when the pocket floor 6 is level with or elevated above the die roll surface (as shown in FIG. 4A or 4B, respectively), the other components of the pocket 3 and the landing surface 5 can be configured as described herein.

For example, the die roll 1 can comprise a die roll surface 2, along with a pocket 3 as shown in FIGS. 4A and 4B. The pocket 3 can be defined by a pocket floor 6, an interior sidewall surface 7, a chamfer 8, and an exterior sidewall surface 9. In various aspects, the floor can be level or elevated above the die roll surface 2, and the interior sidewall surface 7 can be connected to the pocket floor 6 and extending above the die roll surface 2 to the chamfer 8. The die roll 1 of this example further comprises a landing surface 5, the landing surface 5 being elevated from the die role surface 2 and connecting the chamfer 8 to the exterior sidewall surface 9 of the pocket 3. The landing surface 5 can be tapered inwardly towards the pocket floor 6 and forms a boundary of the pocket 3, for example.

Figure 5B:
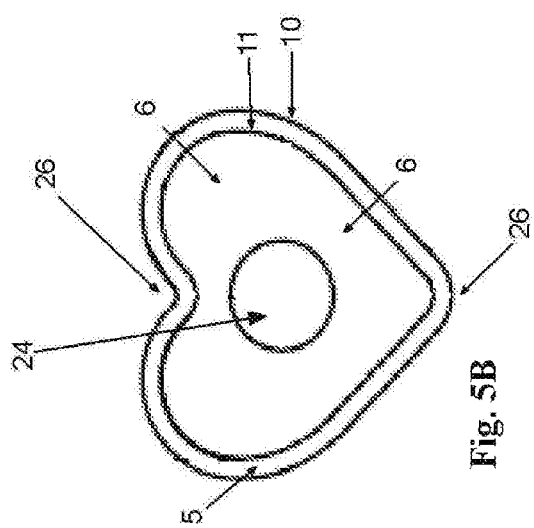
FIG. 5B an illustration depicting a top view of an example pocket of the die roll, in accordance with certain example embodiments.
Figure 5A:
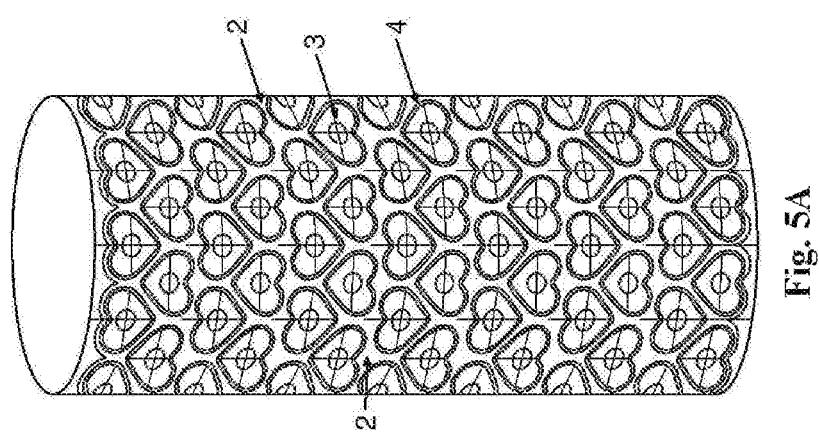
FIG. 5A is an illustration depicting an example configuration of pockets disposed on a die roll surface, in accordance with certain example embodiments.

FIG. 5A is an illustration depicting an example configuration of a plurality of die roll pockets 3 defined on a die roll surface 2, in accordance with the example embodiments. As shown, multiple heart-shaped pockets 3 are configured on the die roll surface 2, the die roll surface 2 being interspersed among the multiple pockets 3. A landing surface 5 (FIG. 5B) of a land 4 circumscribes each pocket 3 in the shape of a heart, thus forming the heart-shaped pocket 3. Each of the multiple pockets 3 are configured, for example, to maximize the number of pockets 3 on the die roll surface 2.

FIG. 5B is an illustration depicting a top view of an example pocket 3 of the die roll 1, in accordance with certain example embodiments. For example, one or more of the pockets of FIG. 5B may be disposed upon the die roll 1 of FIG. 5A. In the example pocket 3 of FIG. 5B, the boundary defined by the landing surface 5 is in the shape of a heart, the heart having a point 26 at the bottom. The example heart-shaped pocket 3 also has a floor 6 and a vent opening 24. The landing surface 5 also has an exterior edge 10 and an interior edge 11 that form the boundaries of the landing surface of the land 4. As is shown in FIG. 5B, the landing surface 5 runs along the border of the pocket 3. For example, the exterior edge 10 of the landing surface 5 runs along the exterior border of the pocket 3, while the interior edge 11 of the landing surface 5 runs along the interior border of the pocket 3.

Figure 6B:
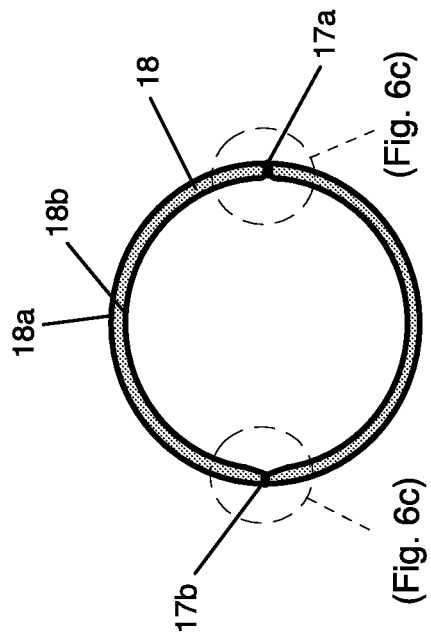
FIG. 6B is cross-sectional view of an example softgel, illustrating the profile taken through the line 6B-6B as shown in FIG. 6A, in accordance with certain example embodiments.
Figure 6C:
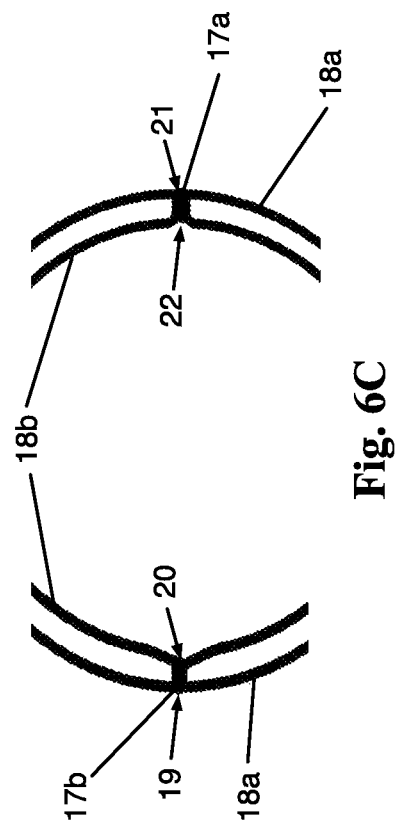
FIG. 6C is an enlarged view of the leading edge of the seam and the trailing edge of the seam (as indicated on FIG. 6B), in accordance with certain example embodiments.
Figure 6A:
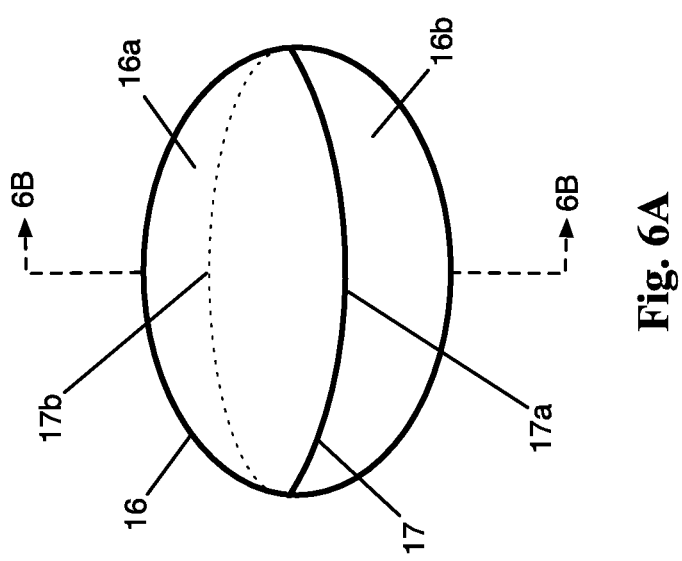
FIG. 6A is an illustration depicting an example softgel, in accordance with certain example embodiments.

FIG. 6A is an illustration depicting an example softgel 16, in accordance with certain example embodiments. For example, the softgel 16 can be produced with a die roll 1 as described herein and in accordance with the methods described herein. The softgel 16 comprises two complementary softgel halves, such as a top shell 16a (a first shell half) and a bottom shell 16b (a second shell half). The top shell 16a and the bottom shell 16b, for example, come together at a seam 17, for example, to form the softgel 16. The seam 17, for example, represents the region or juncture of the softgel 16 where the top shell 16a and a bottom shell 16b are sealed together during the softgel 16 manufacturing process. Thus, in the finished softgel product, the seam 17, for example, circumscribes the circumference of the softgel 16 between the top shell 16a and the bottom shell 16b. In the example softgel 16 shown in FIG. 6A, a leading edge 17a of the seam 17 is also depicted. Also depicted (as the dotted, out-of-sight line) is the trailing edge 17b of the seam 17.

As those skilled in the art will appreciate, the leading edge 17a of the seam 17 is formed, for example, from the portion of the gelatin ribbons that first enter die rolls during the softgel manufacturing process. The trailing edge 17b of the seam 17 is formed, for example, from the portion of the gelatin ribbons that trail behind the portions of the gelatin film that form the leading edge 17a. For example, during the manufacturing process, the sealing of the two softgel halves (16a and 16b) together occurs progressively from the leading edge 17a of the seam 17 to the trailing edge 17b of the seam as the gelatin films progress through the mated die rolls.

FIG. 6B is cross-sectional view of an example softgel 16, illustrating the profile taken through the line 6B-6B as shown in FIG. 6A, in accordance with certain example embodiments. In addition to the cross-section through the leading edge 17a of the seam 17 and the trailing edge 17b of the seam 17, also shown is the softgel wall 18 of the softgel. The softgel wall 18, for example, includes an outer wall 18a and an inner wall 18b, the outer wall 18a representing the outside surface of the softgel 16 and the inner wall 18b representing the inside surface of the softgel 16. For example, the inner wall 18b is the surface of the softgel that is in contact with the fill material as described herein, whereas the outer wall 18a represents the outside surface of the softgel. The components of the softgel wall 18, including the seam 17 components and the softgel wall 18 components, are made of the gelatin material as described herein, for example. That is, the softgel wall 18 and the seam 17 include the solid yet flexible gel material that is cut from the gelatin ribbons as described herein.

The softgel wall 18 of the softgel 16 has a thickness that can be determined, for example, by selecting a point on the wall 18 and measuring the distance from the outer wall 18a surface to the inner wall 18b surface. For example, the softgel wall thickness can be determined by measuring the wall thickness on either half of the softgel shell. As those skilled in the art will appreciate, the thickness of the softgel wall 18 can be determined and configured by a number of factors, such as the gelatin formulation used to make the ribbons, the thickness of the ribbons, and the drying and curing of the softgels 16. In certain example embodiments, the thickness of the softgel wall 18 can be about 0.1 to about 1.5 mm, such as about 0.1, 0.2, 0.3, 0.4, 0.5, 0.6, 0.7, 0.8, 0.9, 1.0, 1.1, 1.2, 1.3, 1.4, or 1.5 mm. In certain example embodiments, the thickness of the softgel wall 18 can be about 30 to about 40 thousandths of an inch, such as about 32.0 to 36.0 thousandths of an inch.

FIG. 6C is an enlarged view of the leading edge 17a of the seam 17 and the trailing edge 17b of the seam 17 (as indicated on FIG. 6B), in accordance with certain example embodiments. The seam 17 has a thickness that can be determined, for example, by measuring the distance between the outer seam edge and the inner seam edge, the outer seam edge representing the portion of the seam 17 on the outside of the softgel 16, while the inner seam edge represents the portion of the seam 17 that is on the inside of the softgel 16 and hence in contact with any fill material. For example, the thickness of trailing edge 17b of the seam 17 can be determined by measuring and/or comparing the distance from the trailing edge outer seam edge 19 and the trailing edge inner seam edge 20. Likewise, the thickness of leading edge 17a of the seam 17 can be determined, for example, by measuring and/or comparing the distance from the leading edge outer seam edge 21 and the leading edge inner seam edge 22.

In certain example embodiments, the softgel 16 has a seam 17 thickness that is a fraction of the thickness of the wall 18. For example, a softgel 16, such as a softgel made with a die roll 1 as configured herein and made in accordance with the methods and processes described herein, can have a seam 17 thickness that is at least about 35, 40, 45, 50, 55, 60, 65, 70, 75, 80, 85, 90 or 95% of the thickness of the softgel wall 18 thickness along the length of the seam 17 as the seam 17 circumscribes the softgel 16 as described herein. In certain example embodiments, the thickness of the seam 17 varies along the length of the seam 17, such as within the percentages identified above. For example, at least one region of the seam 17 can be about 40% to 60% of the wall thickness, whereas at least one other region of the seam 17 can be about 50% to 70% of the softgel wall 18 thickness. Optionally, at least one other region of the seam 17 can be about 60% to 90% the thickness of the softgel wall 18.

In certain example embodiments, the softgel 16 has a thickness of the trailing edge 17b of the seam (that is, a trailing edge thickness) that is a fraction of the softgel wall 18 thickness. For example, a softgel 16, such as a softgel made with a die roll 1 as configured herein and made in accordance with the methods and processes described herein, can have a trailing edge 17b thickness that is at least about 35, 40, 45, 50, 55, 60, 65, 70, 75, 80, 85, 90 or 95% of the thickness of the softgel wall 18 thickness. In certain example embodiments, the softgel 16 has a trailing edge 17b thickness of between about 35% to 65% of the softgel wall 18 thickness, such as about 35, 40, 45, 50, 55, 60, or 65% of the softgel wall 18 thickness. In certain example embodiments, the thickness of the trailing edge 17b varies along the length of the trailing edge 17b, such as within the percentages identified herein.

In certain example embodiments, the softgel 16 has a thickness of the leading edge 17a of the seam (that is, a leading edge thickness) that is a fraction of the softgel wall 18 thickness. For example, a softgel 16, such as a softgel made with a die roll 1 as configured herein and made in accordance with the methods and processes described herein, has a leading edge 17a thickness that is at least about 35, 40, 45, 50, 55, 60, 65, 70, 75, 80, 85, 90 or 95% of the thickness of the softgel wall 18 thickness. In certain example embodiments, the softgel 16 has a leading edge 17a thickness of between about 80% to 95% of the softgel wall 18 thickness, such as about 80, 85, 90, or 95% of the softgel wall 18 thickness. In certain example embodiments, the thickness of the leading edge 17a varies along the length of the leading edge 17a, such as within the percentages identified above.

Figure 7:
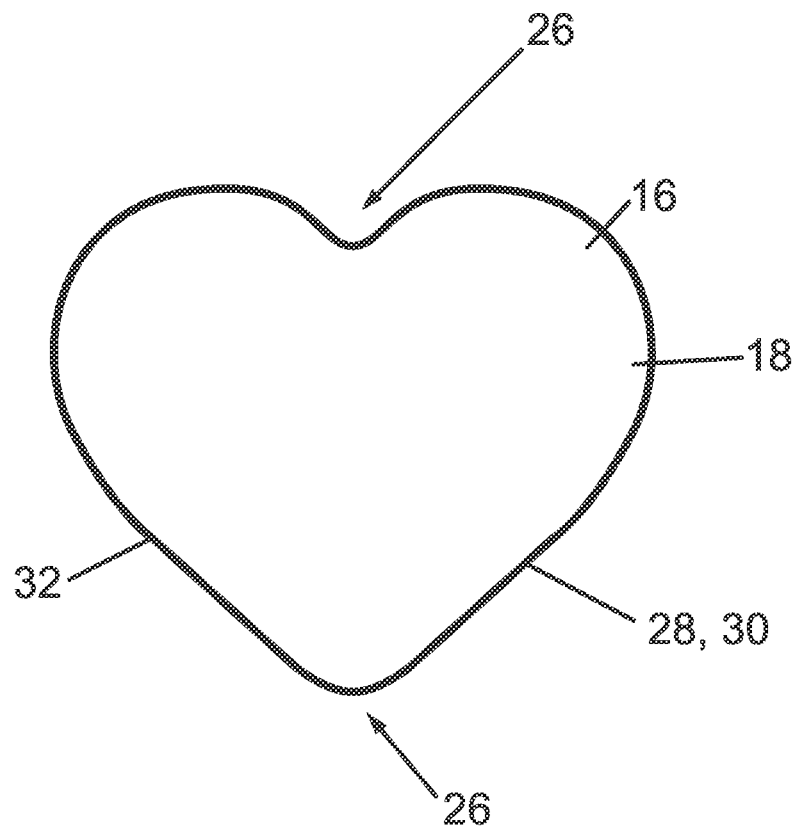
FIG. 7 is an illustration depicting a top plan view of an example softgel, in accordance with certain example embodiments.

While the example softgel 16 illustrated in FIG. 6A-6C is rounded and oblong, it will be appreciated that softgels of various predetermined shapes can be made in accordance with the apparatus, methods, and processes described herein. Some of the shapes, such as a heart shaped softgel (see FIG. 7) can have at least one point 26 formed at the intersection of two or more straight or substantially straight seam portions 28 when viewed from above, as in FIG. 7. In one aspect, at least two portions of the seam can be substantially linear. For example, the softgel can have a first linear seam portion 30 at an acute angle to a second linear 32 seam portion. In another example, the first linear seam portion of the softgel can be substantially normal to the second linear seam portion. The point formed between the linear portions of the seam can be a fine point, or be slightly rounded. That is, the softgel of the current application can have at least one point or non-rounded seam. Thus, the softgel as described herein can be circular or oval in cross-sectional shape (as with conventional softgels). However, the softgel of the current application can also comprise at least one point and/or other angle. For example, the softgel can also be substantially square, rectangular, triangular, and the like in cross-sectional shape. In other examples, the softgel can comprise any shape having two or more substantially linear seam portions, such as the heart shape of FIG. 7.

In addition to the die roll 1 and softgel 16 provided herein, also provided is a method and process for manufacturing the softgels, such as with the die roll 1 described herein. For example, soft film ribbons of gelatin are formed from a film-forming composition. That is, the film-forming composition used to prepare the softgels 16 can be prepared according to formulations known to those of skill in the art. The film-forming composition can be any suitable composition for making softgels. The properties of the film-forming composition are determined, at least in part, by the cohesive strength of the constituent gelatin, expressed as "bloom." In certain example embodiments, the gelatin film formulation includes 219.0 kg of gelatin 150 bloom, 110.0 kg of glycerin 99.5%, and 172.5 kg of purified water and 6.5 kg of caramel color. In certain example embodiments, the gelatin film formulation includes between about 37% and about 41% 150 bloom gelatin, such as bloom bovine gelatin, between about 17% and about 21% glycerin and between about 25% and about 29% water.

In certain example embodiments, preparing the gelatin film includes pre-weighing all raw materials into clean containers, adding glycerin and purified water to a gelatin melter (which is set in an example embodiment to 176° F.), and then mixing the material until the material reaches 176° F. At that point, pre-weighed raw gelatin is added. A vacuum is then applied to allow the liquids to rise and saturate the gelatin. The vacuum is removed, the tank with the mixture is sealed with the vacuum. The mixture is then allowed to mix for about 30 minutes in/on a mixer/agitator, and the gelatin is de-aerated. The vacuum valve on the gelatin melter is left closed to seal the vacuum and the vacuum pump is turned off. The gelatin is then allowed to mix under sealed vacuum for 10 minutes at slow mixing speed, or until the temperature is between about 149° F. to about 158° F.

Once the gelatin mixture is prepared, such as described herein, the gelatin films are formed into ribbons by methods known to those skilled in the art, such as via a rotary die process. The ribbons are then fed through two mated die rolls 1 of a gelatin encapsulation machine. For example, two gelatin ribbons are supplied to and between a pair of rotating and mated die rolls from the upper side of the dies rolls, one from the right and one from the left, the die rolls 1 being configured as described herein. The two mated roll dies are close to and confront each other. A softgel 16 containing two half-capsule (16a and 16b) shells is formed by closing in the rotating dies rolls. A liquid fill composition is injected into the interior of the softgel 16 with pressure to convert the otherwise flat softgel body into a swollen body of the softgel 16.

The fill material can be any material known in the art, such as those commonly included in softgels. For example, the fill material can include a liquid carrier and active ingredient, the active ingredient being suspended within the liquid carrier. In certain example embodiments, the liquid carrier is a water-immiscible liquid, such as a vegetable and/or aromatic oil, an aromatic and aliphatic and aliphatic hydrocarbon, a chlorinated hydrocarbon, an ether, an ester, high molecular weight organic acid and/or alcohol, or lower molecular weight polyalkylene glycol. Other embodiments can contain water-miscible liquid carriers as well. The active ingredient can include any medicaments, vitamins, minerals, fruits, herbals, and/or other encapsulatable materials or combinations thereof understood by those skilled in the art to support a desired effect. For example, if the effect desired is mineral supplementation, exemplary active ingredients can be calcium, magnesium and Vitamin D. In certain example embodiments, the active ingredient can include krill oil, salmon oil, and/or flax seed oil, such as highly purified flax seed oil.

Additionally or alternatively, if the desired effect is targeted toward urinary tract health, an example active ingredient of cranberry, such as cranberry extract, is included. If the desired effect is heart health, the active ingredient can include an emulsified fatty acid, such as an emulsified omega-3 or omega-7 fatty acid. In certain example embodiments, the active ingredient is palmitoleic acid. In certain example embodiments, the active ingredient is Omega-9. In certain example embodiments, the active ingredient is hyaluronic acid. The fill material can also include other ingredients, such as sweeteners and other flavorants, or flavor modifiers. Suitable flavor modifiers can include any natural or artificial flavor or a combination thereof. In certain example embodiments, the active ingredient will be present in an amount of from up to about 50% by weight, with variations allowed for the variable fill employed. Mixtures of active ingredients can also be incorporated into the fill.

With the injection of the fill material, the body of the softgel 16 swells into the pocket 3, for example, thereby taking the form of the pocket 3. The softgel product is then dried and cured to produce a final softgel product. The drying and curing process can be accomplished by a variety of known methods. For example, the drying and curing process can be accomplished as described in U.S. Pat. No. 8,621,764, the contents of which is expressly hereby incorporated by reference in its entirety.

For example, the drying method includes dividing a space into first, second and third zones and providing a first air handler unit for discharging air into the first zone. The first zone includes a first temperature sensor and a first humidity sensor that are both in communication with the first air handler unit. A second air handler unit is provided for discharging air into the second zone, the second zone including a second temperature sensor and a second humidity sensor that are both in communication with the second air handler unit. A third air handler unit is also provided for discharging air into the third zone. The third zone includes a third temperature sensor and a third humidity sensor that are both in communication with the third air handler unit.

The method further includes, for example, providing air to the first air handler unit at a first temperature and a first relative humidity, wherein the air within the first air handler unit is conditioned such that it has a second temperature and a second relative humidity. The conditioned air is blown from the first air handler unit into the first zone. Air is provided to the second air handler unit at the first temperature and the first relative humidity. The air within the second air handler unit is conditioned such that it has a third temperature and a third relative humidity, the conditioned air being blown from the second air handler unit into the second zone. The method further includes providing air to the third air handler unit at the first temperature and the first relative humidity, the air within the third air handler unit being conditioned such that it has a fourth temperature and a fourth relative humidity. The conditioned air is blown from the third air handler unit into the third zone. The method further includes, for example, providing a series of tumble dryers that extends from the first zone, through the second zone and into the third, and drying the gelatin capsules by moving the gelatin capsules through the tumble dryers from the first zone to the third zone.

In certain example embodiments, the second temperature is between about 50° F. and about 68° F. and the second relative humidity is between about 19% and about 23%. The third temperature is between about 72° F. and about 87° F. and the third relative humidity is between about 9% and about 14%. The fourth temperature is between about 68° F. and about 74° F. and the fourth relative humidity is between about 10% and about 15%.

In certain example embodiments, the second temperature is between about 59° F. and about 61° F. and the second relative humidity is between about 20.5% and about 21.5%. The third temperature is between about 81° F. and about 83° F. and the third relative humidity is between about 10.5% and about 11.5%. The fourth temperature is between about 71° F. and about 73° F. and the fourth relative humidity is between about 12.5% and about 13.5%.

In certain example embodiments, the second temperature is about 60° F. and the second relative humidity is about 21%. The third temperature is about 82° F. and the third relative humidity is about 11%. The fourth temperature is about 72° F. and the fourth relative humidity is about 13%.

In certain example embodiments, the air provided to the first, second, and third air handler units has a first dew point. The air within the first air handler unit is conditioned such that it has a second dew point, the air within the second air handler unit is conditioned such that it has a third dew point, and the air within the third air handler unit is conditioned such that it has a fourth dew point. For example, the second dew point is between about 15° F. and about 30° F., the third dew point is between about 15° F. and about 23° F., and the fourth dew point is between about 15° F. and about 23° F.

In certain example embodiments, the first air handler unit releases the conditioned air into the first zone at between about 3000 CFM and about 6000 CFM. The second air handler unit releases the conditioned air into the second zone at between about 2500 CFM and about 5000 CFM. The third air handler unit releases the conditioned air into the third zone at between about 1000 CFM and about 3000 CFM.

In certain example embodiments, the softgels 16 can be dried to a hardness of eight newtons in about thirteen hours. In certain example embodiments, the first, second, and third air handler units are positioned within the first, second, and third zones, respectively. In certain example embodiments, the air provided to the first, second, and third air handler units is provided by a HVAC unit that is positioned outside of the first, second, and third zones.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the art will recognize and understand. For example, while processes can be presented in a given order, alternative embodiments can perform routines having steps in a different order, with some steps being deleted, moved, added, subdivided, combined, and/or modified to provide alternative or sub-combinations. Each of these processes can be implemented in a variety of different ways, as those skilled in the art will appreciate. Also, while processes are at times shown as being performed in series, these processes can instead be performed in parallel, or can be performed, at different times. Further any specific numbers noted herein are only examples—alternative implementations can employ differing values or ranges.

The teachings of the disclosure provided herein can be applied to other systems, not necessarily the system described above. The elements and acts of the various embodiments described above can be combined to provide further embodiments. Any patents noted above that are incorporated herein by reference, for example, can be modified, as necessary, to provide yet further embodiments of the disclosure provided herein. Further, while the above description describes certain embodiments, the teachings can be practiced in many ways that will be appreciated by those of skill in the art no matter how detailed the above appears in text. Details of the die roll and related processes and products can vary considerably in their implementation details, while still being encompassed by the subject matter disclosed herein. Hence, although example embodiments of the invention have been shown and described, it is to be understood that all the terms used herein are descriptive rather than limiting, and that many changes, modifications, and substitutions can be made by one having skill in the art without departing from the spirit and scope of the claims below.

What is claimed is:

1. A softgel, comprising:
a first softgel shell half and a second softgel shell half, the softgel shell halves being complementary to each other and each softgel shell half comprising a softgel wall having an interior wall surface and an opposed exterior wall surface, the softgel wall of each softgel shell half comprising a softgel wall thickness corresponding to a distance between the interior wall surface and the exterior wall surface, wherein the softgel wall thickness is at least 0.7 mm thick;
a seam formed at a juncture of the first softgel shell half and the second softgel shell half, wherein the seam comprises a plurality of substantially linear seam portions when viewed from above, the plurality of substantially linear seam portions comprising a first linear seam portion that is at an angle relative to a second linear seam portion of the plurality of substantially linear seam portion, and
wherein the seam comprises a leading edge and an opposed trailing edge, wherein the trailing edge has a trailing edge thickness corresponding to a distance from an outer seam edge of the trailing edge and an inner seam edge of the trailing edge, the trailing edge thickness being greater than 20% of the softgel wall thickness of at least one of the first softgel shell half and the second softgel shell half.

2. The softgel of claim 1, wherein the trailing edge thickness is at least 25% of the softgel wall thickness of at least one of the first softgel shell half and the second softgel shell half.

3. The softgel of claim 1, wherein the trailing edge thickness is at least 30% of the softgel wall thickness of at least one of the first softgel shell half and the second softgel shell half.

4. The softgel of claim 1, wherein the trailing edge thickness is at least 35% of the softgel wall thickness of at least one of the first softgel shell half and the second softgel shell half.

5. The softgel of claim 1, wherein the leading edge has a leading edge thickness corresponding to a distance between a leading edge outer seam edge and a leading edge inner seam edge, and wherein the leading edge thickness is greater than 20% of the softgel wall thickness of at least one of the first softgel shell half and the second softgel shell half.

6. The softgel of claim 5, wherein the leading edge thickness is at least 25% of the softgel wall thickness of at least one of the first softgel shell half and the second softgel shell half and wherein the wall thickness is at least 0.8 mm thick.

7. The softgel of claim 5, wherein the leading edge thickness is at least 30% of the softgel wall thickness of at least one of the first softgel shell half and the second softgel shell half.

8. The softgel of claim 5, wherein the leading edge thickness is at least 35% of the softgel wall thickness of at least one of the first softgel shell half and the second softgel shell half.

9. The softgel of claim 1, wherein a substantially rounded point is formed at an intersection of the first linear seam portion and the second linear seam portion.

10. A softgel, comprising:
a softgel wall, the softgel wall comprising a softgel wall thickness corresponding to a distance between an interior wall surface of the softgel wall and an exterior wall surface of the softgel wall, wherein the softgel wall thickness is at least 0.7 mm thick; and,
a seam that circumscribes the circumference of the softgel, wherein the seam comprises a seam thickness corresponding to a distance between an outer seam edge of the seam and an inner seam edge of the seam, the seam thickness being greater than 30% of the softgel wall thickness along the length of the seam.

11. The softgel of claim 10, wherein the seam thickness is at least 35% of the softgel wall thickness along the length of the seam.

12. The softgel of claim 10, wherein the seam thickness is at least 40% of the softgel wall thickness along the length of the seam.

13. The softgel of claim 10, wherein the softgel wall thickness is at least 0.8 mm thick.

14. The softgel of claim 10, wherein the seam further comprises a trailing edge, the trailing edge comprising a trailing edge thickness corresponding to a distance from an outer seam edge of the trailing edge and an inner seam edge of the trailing edge, the trailing edge thickness being greater than 25% of the softgel wall thickness.

15. The softgel of claim 14, wherein the trailing edge thickness is at least 35% of the softgel wall thickness.

16. A softgel, comprising:
a first softgel shell half and a second softgel shell half, each softgel half being complementary to each other and comprising a softgel wall thickness corresponding to a distance between an interior wall surface and an exterior wall surface of the softgel halves, wherein the softgel wall thickness is at least 0.7 mm thick; and
a seam formed at a juncture of the first softgel shell half and the second softgel shell half, the seam comprising a leading edge and an opposed trailing edge,
wherein the trailing edge comprises a trailing edge thickness corresponding to a distance from an outer seam edge of the trailing edge and an inner seam edge of the trailing edge, the trailing edge thickness being greater than 20% of the softgel wall thickness of at least one of the first softgel shell half and the second softgel shell half and
wherein the seam otherwise comprises a seam thickness along the length of the seam that is at least 30% of the softgel wall thickness of at least one of the first softgel shell half and the second softgel shell half.

17. The softgel of claim 16, wherein the seam thickness is at least 30% of the softgel wall thickness of at least one of the first softgel shell half and the second softgel shell half along the length of the seam.

18. The softgel of claim 16, wherein trailing edge thickness is at least 30% of the softgel wall thickness of at least one of the first softgel shell half and the second softgel shell half.

19. The softgel of claim 16, wherein the trailing edge thickness is at least 25% of the softgel wall thickness of at least one of the first softgel shell half and the second softgel shell half and wherein the seam thickness is otherwise at least 30% of the softgel wall thickness of at least one of the first softgel shell half and the second softgel shell half along the length of the seam.

20. The softgel of claim 16, wherein the leading edge has a leading edge thickness corresponding to a distance between a leading edge outer seam edge and a leading edge inner seam edge, wherein the leading edge thickness is greater than 20% of the softgel wall thickness of at least one of the first softgel shell half and the second softgel shell half, wherein the trailing edge thickness is greater than 20% of the softgel wall thickness of at least one of the first softgel shell half and the second softgel shell half, and wherein the seam otherwise comprises a seam thickness that is greater than 30% of the softgel wall thickness of at least one of the first softgel shell half and the second softgel shell half.

* * * * *